United States Patent [19]
Jones et al.

[11] Patent Number: 6,005,135
[45] Date of Patent: Dec. 21, 1999

[54] WATER-BORNE POLYMERIC VEHICLE FOR COATING COMPOSITIONS CONTAINING AN AMINE OR AMMONIUM SALT OF PHENOLIC ESTER ALCOHOLS

[75] Inventors: Frank N. Jones, Ann Arbor; Ramachandran P. Subrayan, Ypsilanti, both of Mich.

[73] Assignee: Exxon Chemical Patents Inc., Houston, Tex.

[21] Appl. No.: 08/630,403

[22] Filed: Mar. 21, 1996

[51] Int. Cl.$^6$ .......................... C07C 69/76; C07C 69/03; C07C 69/66

[52] U.S. Cl. ................................. 560/55; 560/60; 560/64; 560/76; 560/81; 560/85; 560/103; 560/105

[58] Field of Search .................................. 560/103, 105, 560/55, 60, 64, 76, 81, 85

[56] References Cited

U.S. PATENT DOCUMENTS

| | | |
|---|---|---|
| 3,409,579 | 11/1968 | Robins . |
| 3,789,044 | 1/1974 | Taft et al. . |
| 3,836,491 | 9/1974 | Taft et al. . |
| 4,031,068 | 6/1977 | Cantor . |
| 4,130,549 | 12/1978 | Ueno et al. ................................ 528/93 |
| 4,147,679 | 4/1979 | Scriven et al. . |
| 4,318,833 | 3/1982 | Guagliardo ............................... 524/457 |
| 4,331,782 | 5/1982 | Linden ..................................... 525/173 |
| 4,343,839 | 8/1982 | Blegan .................................... 427/340 |
| 4,365,039 | 12/1982 | Blegan .................................... 524/773 |
| 4,374,167 | 2/1983 | Blegan .................................... 428/141 |
| 4,374,181 | 2/1983 | Blegen .............................. 428/423.3 |
| 4,737,565 | 4/1988 | Goel ......................................... 528/73 |
| 4,877,838 | 10/1989 | Toman ..................................... 525/107 |
| 4,888,441 | 12/1989 | Calbo, Jr. et al. ...................... 560/198 |
| 4,922,002 | 5/1990 | Calbo, Jr. et al. ...................... 528/286 |
| 4,927,876 | 5/1990 | Coogan et al. .......................... 524/457 |
| 5,019,100 | 5/1991 | Hennink et al. ............................. 623/6 |
| 5,166,289 | 11/1992 | Yezrielev et al. ....................... 525/443 |
| 5,210,155 | 5/1993 | Yezrielev et al. ....................... 525/442 |
| 5,235,006 | 8/1993 | Jones et al. ............................. 525/510 |
| 5,239,018 | 8/1993 | Yezrielev et al. ....................... 525/418 |
| 5,322,884 | 6/1994 | Wellman et al. ....................... 524/601 |
| 5,326,831 | 7/1994 | Yezrielev et al. ....................... 525/437 |
| 5,334,652 | 8/1994 | Wellman et al. ....................... 524/601 |
| 5,334,671 | 8/1994 | Yezrielev et al. ....................... 525/443 |
| 5,453,469 | 9/1995 | Yezrielev et al. ....................... 525/418 |
| 5,458,920 | 10/1995 | Yezrielev et al. .................... 427/385.5 |
| 5,508,340 | 4/1996 | Hart ....................................... 524/591 |
| 5,681,906 | 10/1997 | Yezrielev et al. ....................... 525/450 |
| 5,763,529 | 6/1998 | Lucas ..................................... 524/507 |

FOREIGN PATENT DOCUMENTS

| | | |
|---|---|---|
| 0419088 | 3/1991 | European Pat. Off. . |
| 2809768 | 9/1978 | Germany . |
| 54-87753 | 7/1979 | Japan . |
| 05155840 | 6/1993 | Japan . |
| 1290848 | 9/1972 | United Kingdom . |
| 1518683 | 7/1978 | United Kingdom . |

OTHER PUBLICATIONS

Stumpe et al., "Deactivation of Excited States in Polyurethanes by Energy Transfer to Salicylic Acid Derivatives and its Application to the Photo–stabilisation of Polyurethanes", Polymer Degradation and Stability 17 (1987) 103–115.

Watanabe, CAPLUS AN 1980: 23539, Abstracting JP 54087753.

*Primary Examiner*—Jeffrey C. Mullis
*Attorney, Agent, or Firm*—Fitch, Even, Tabin & Flannery

[57] ABSTRACT

Water-borne polymeric vehicles are described where the polymeric vehicle includes the amine or ammonium salt of a phenolic ester alcohol.

20 Claims, No Drawings

WATER-BORNE POLYMERIC VEHICLE FOR COATING COMPOSITIONS CONTAINING AN AMINE OR AMMONIUM SALT OF PHENOLIC ESTER ALCOHOLS

This invention is directed to polymeric vehicles and formulated coating compositions for paint coating binders. The polymeric vehicles and formulated coating compositions use water to effect viscosities which permit the application of such polymeric vehicles or formulated coating compositions by existing commercial application equipment. More particularly, this invention is directed to polymeric vehicles and formulated coating compositions which include at least one water reducible polymer or water-thinnable oligomer or polyol and at least one amine salt of a phenolic ester alcohol. These compositions are very low in volatile organic compounds, and provide a coating binder with extremely good film properties. Further, this invention also is directed to controlling the viscosities of the afore-described polymeric vehicle and formulated coating composition as well as controlling or reducing volatile organic compounds (VOCs) emanating from such compositions.

DESCRIPTION OF THE PRIOR ART AND BACKGROUND

One of the primary components in paint is the "film former" that provides a film for the protective function for a substrate coated with the paint. Film forming components of liquid paints include resins which have required organic solvents to provide the resins with suitable viscosities such that the paint can be applied by existing commercial application equipment. Use of organic solvents, however, raises at least two problems. In the past and potentially in the future, petrochemical shortages mitigate against the use of organic solvent in great volumes. Second, environmental concern mitigates against the use of organic solvents and requires such use be minimized.

Environmental concern has become increasingly important. This concern not only extends to preservation of the environment for its own sake, but extends to public safety as to both living and working conditions. Volatile organic emissions resulting from coating compositions which are applied and used by industry and by the consuming public are not only often unpleasant, but also contribute to photochemical smog. Governments have established regulations setting forth guidelines relating to VOCs which may be released to the atmosphere. The U.S. Environmental Protection Agency (EPA) has established guidelines limiting the amount of VOCs released to the atmosphere, such guidelines being scheduled for adoption or having been adopted by various states of the United States. Guidelines relating to VOCs, such as those of the EPA, and environmental concerns are particularly pertinent to the paint and industrial coating industry which uses organic solvents which are emitted into the atmosphere.

To reduce organic solvent content and VOCS, researchers have developed high solids coating compositions, water-borne coating compositions and powdered coating compositions. High solids compositions generally are liquid and are designed to minimize solvents. Powdered coating compositions are solid powders and generally eliminate solvents. Water-borne coating compositions use water to reduce VOCs. While each have advantages, each coating composition has disadvantages.

Coating compositions which include high solids polymeric vehicles based upon polyesters have become popular. Typically these compositions require the use of some organic solvents. In high solid polyesters as opposed to "conventional" compositions which use organic solvents, high molecular weight generally needs to be achieved during crosslinking rather than being attained from the basic polyester polymer. Hence, high solids polyesters normally supply a greater number of reactive sites (predominantly hydroxyl groups) available for crosslinking. The resultant polymers typically exhibit 70–80% solids-weight when reacted stoichiometrically with isocyanate crosslinkers, but frequently yield empirical solids up to 12% lower, when crosslinked with melamine resins. Despite their reduced use of organic solvents, high solids polyester coating compositions can be produced on the same equipment and are employed in many of the same applications as lower solids "conventional" polyester coating compositions. Further, as a result of their many strengths such as ease of manufacturing and use, low volatile emissions, reduced energy requirements, greater application efficiency, lower handling and storage costs, and excellent physical properties, high solids polyester coating compositions have enjoyed spectacular growth in manufacture and use. They still require organic solvents, however, and are a source of VOCs.

Powder coatings and UV-curable coatings are desirable ultrahigh or 100% solids coatings. However, there are limitations as to the technique and the equipment which are used to apply the powdered composition.

Another way to reduce VOCs is to use water as a medium for the film-forming components in the polymeric vehicle. One way is to make a polymer such as a polyester, alkyd, acrylic or epoxy polymer having carboxyl groups and acid number in amounts effective such that when the carboxyl groups are neutralized, they will permit the polymer or oligomer to be dispersed in a mixed solvent system which includes an organic solvent and water. The amine salt of the oligomer or polymer disperses into the mixed water/organic solvent system with the formulation of a dispersion as opposed to a solution. This is a water reducible system.

Another way to reduce VOCs using water is to actually make a solution of polyols which may be oligoesters or acrylic oligomers having hydroxyl groups and a number average molecular weight of less than about 10,000. The hydroxyl number of the oligomer is sufficiently high and effective for permitting the formation of a solution of the oligomer in water or a mixed solvent system of water and organic solvent. This is a water-thinnable polymeric vehicle.

An object of the invention is to provide a polymeric vehicle which will reduce or eliminate VOCs.

Another object of this invention is to provide a hardener for use in a water-reducible or water-thinnable polymeric vehicle or formulated coating composition.

Another object of this invention is to provide polymeric vehicles which are not only low in VOCs, but which provide coating binders with good film properties such as hardness and impact resistance.

Yet another object of this invention is to control the viscosity to low levels at a specific shear rate of a liquid polymeric vehicle or liquid formulated coating composition with the use of water and with the minimization of organic solvents for such control.

Further, objects and advantages of the invention will be found by reference to the following description.

SUMMARY OF THE INVENTION

The invention provides an amine salt of a phenolic ester alcohol and a water-reducible or water-thinnable polymeric vehicle which includes the latter amine salt.

The polymeric vehicle of the invention is effective for providing an aqueous high solids polymeric vehicle or formulated coating composition which has at least 3 weight percent water, based upon the weight of the formulated coating composition. The amine or ammonia salt of the phenolic ester alcohol not only serves as a hardener for the polymeric vehicle, because it is a salt, it may be used as a hardener in an aqueous system. The phenolic ester alcohol which is a precursor to the amine or ammonia salt has at least one phenolic hydroxyl group and at least one aliphatic hydroxyl group, the hydrogen on the phenolic hydroxyl group being reactive with ammonia or amine to form the amine salt. In an important aspect, the phenolic ester alcohol has about one aliphatic hydroxyl group. In an important aspect, the amine or ammonia salt of the phenolic ester alcohol has the general formula A

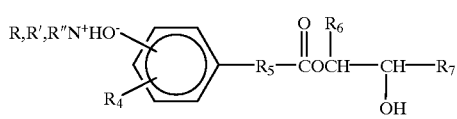

A wherein $R_4$ is selected from the group consisting of hydrogen, halogen, hydroxyl, R, R', $R''N^+HO^-$, $C_1$ to $C_8$ alkyl and $C_1$ to $C_8$ alkoxy, $R_5$ is a direct bond or a $C_1$ to $C_{20}$ organic radical which may incorporate another phenol, aliphatic hydroxyl, ester, ether and/or carbonate group in its structure, $R_6$ is hydrogen or a $C_1$ to $C_{20}$ organic radical which may include an ester group, or a direct bond which may form with $R_7$ part of a 5 or 6 carbon atom cyclic ring structure, $R_7$ is $CH_2R_8$ wherein $R_8$ is selected from the group consisting of hydroxy, $OR_9$, $OOCR_{10}$ and $R_{11}$ wherein $R_9$, is a primary or secondary aliphatic group containing 3 to 20 carbon atoms which may include one or more ester linkages or an aromatic group containing 6 to 20 carbon atoms, $R_{10}$ is a primary, secondary or tertiary aliphatic group containing 4 to 20 carbon atoms which may include one or more ester linkages or an aromatic group containing 6 to 20 carbon atoms, and $R_{11}$ is a $C_2$ to $C_{20}$ organic radical which may include one or more ester linkages and where the organic radical may form with $R_6$ part of a 5 or 6 carbon atom cyclic ring structure. In a particularly important aspect, the general formula has at least two ester linkages or groups, and in a particularly important aspect, $R_5$ or $R_8$ has the ester groups. The —OH expressly shown in formula A is illustrative of an aliphatic hydroxyl group. R, R', R" may be an alkyl (preferably four carbons or less), hydroxyl substituted alkyl, and H.

As used herein, an ester group means

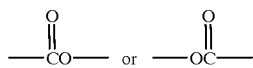

In the water-reducible aspect of the invention, the polymeric vehicle of the invention comprises a blend of an amine or ammonium salt of a polyester, alkyd or acrylic polymer, as well as the amine salt of a phenolic ester alcohol (hereinafter PHEA) which are dispersible in a blend of water and organic solvent. The blend of water and organic solvent will comprise at least 3 weight percent solvent and preferably at least 40 weight percent water.

In the water-thinnable aspect of the invention, the polymeric vehicle comprises a polyol, and/or an oligoester polyol and/or an oligomeric acrylic polyol, as well as the amine or ammonia salt of a PHEA in water or a blend of water and organic solvent. In this aspect the polyol is in solution, but the PHEA salt is dispersed or soluble in the solvent medium.

The water-reducible blend or the water-thinnable blend is mixed with a crosslinker and is cured to form a coating binder. The crosslinker used in the invention is reactive with the carboxyl groups and/or the hydroxyl groups on the polymers, oligomers or polyol in the polymeric vehicle. The crosslinker also must be reactive with the aliphatic hydroxyls on the PHEA and hydrolysis product of the amine salt of the PHEA. In the water-reducible aspect of the invention, the amine salt of the polymer, the amine or ammonia salt of the PHEA and crosslinker are each in amounts effective for providing a coating binder which generally will have a pencil hardness of at least about HB, an impact resistance of at least about 20-inch pounds direct and at least about 20-inch pounds reverse at a film thickness of about 0.5 mil dry.

In the water-thinnable aspect of the invention, the oligomeric polyol or polyol, the amine or ammonia salt of the PHEA and the crosslinker are each in amounts effective to provide a coating binder with the aforedescribed hardness and impact resistance. The crosslinkers used in the invention include amino resins, blocked isocyanates, and mixtures thereof.

In an important aspect, the viscosity of the polymeric vehicle and the formulated coating composition is controlled with an organic solvent which is miscible with water such as an alcohol or acetone, the latter being useful because it is not considered a VOC.

DESCRIPTIONS OF THE PREFERRED EMBODIMENTS

"Polyester" means a polymer which has

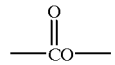

linkages in the main chain of the polymer. "Oligomer" means a compound that is a polymer, but has a number average weight not greater than about 10,000 with or without repeating monomeric units. "Non-oligomeric" is a compound that does not have repeating monomer units along a main chain. "Crosslinker" means a di- or polyfunctional substance containing functional groups that are capable of forming covalent bonds with hydroxyl groups that are present on the oligoester diol and amine or ammonia salt of the PHEA as well as the hydrolysis product of the amine or ammonia salt on the aromatic end of the PHEA. Amino resins and isocyanates are members of this class; melamine resins are a sub-class of amino resins. "Polymeric vehicle" means all polymeric and resinous components in the formulated coating, i.e., before film formation, including but not limited to amine salts of polymers having carboxyl groups neutralized with amine or ammonia, oligoester polyols and the amine salt of the PHEA. "Coating binder" means the polymeric part of the film of the coating after solvent has evaporated after baking and after crosslinking. "Formulated coating composition" means the polymeric vehicle, water and possibly optional organic solvents miscible with water, as well as pigments, catalysts and additives which may optionally be added to impart desirable application characteristics to the formulated coating and desirable properties such as opacity and color to the film.

As used herein, the reaction product of an amine or ammonia with a carboxyl group produces a "salt".

As used herein "high solids" means 75 weight percent solids under ASTM test D-2369-92.

"Polydispersity index" (PDI) means the weight average molecular weight ($M_w$) divided by the number average molecular weight ($M_n$), PDI=$M_w/M_n$.

"VOC" means volatile organic compounds. "Low VOC" means less than about 200 grams VOCs per liter of polymeric vehicle not including water.

"Substantially solventless" means a polymeric vehicle or formulated coating composition having not more than about five weight percent organic solvent.

"Diol" is a compound or oligomer with two hydroxyl groups. "Polyol" is a compound or oligomer with two or more hydroxyl groups. As used in this application, "polymer" means a polymer with repeating monomeric units as defined herein and includes oligomers as defined herein.

"Solvent" means an organic solvent.

"Organic solvent" means a liquid which includes but is not limited to carbon and hydrogen which liquid has a boiling point in the range of from about 30° C. to about 300° C. at about one atmosphere pressure. It does not include the urethane diol.

"Volatile organic compounds" are defined by the U.S. Environmental Protection Agency at 40 C.F.R. 51.000 of the Federal Regulations of the United States of America as any compound of carbon, excluding carbon monoxide, carbon dioxide, carbonic acid, metallic carbides or carbonates, and ammonium carbonate, which participates in atmospheric photochemical reactions.

This includes any such organic compound other than then following, which have been determined to have negligible photochemical reactivity: acetone; methane; ethane; methylene chloride (dichloromethane); 1,1,1-trichloroethane (methyl chloroform); 1,1,1-trichloro-2,2,2-trifluoroethane (CFC-113); trichlorofluoromethane (CFC-11); dichlorodifluoromethane (CFC-12); chlorodifluoromethane (CFC-22); trifluoromethane (FC-23); 1,2-dichloro-1,1,2,2-tetrafluoroethane (CFC-114); chloropentafluoroethane (CFC-115); 1,1,1-trifluoro 2,2-dichloroethane (HCFC-123); 1,1,1,2-tetrafluoroethane (HF-134a); 1,1-dichloro 1-fluoroethane (HCFC-141b); 1-chloro 1,1-difluoroethane (HCFC-142b); 2-chloro-1,1,1,2-tetrafluoroethane (HCFC-124); pentafluoroethane (HFC-125); 1,1,2,2-tetrafluoroethane (HFC-134); 1,1,1-trifluoroethane (HFC-143a); 1,1-difluoroethane (HFC-152a); and perfluorocarbon compounds which fall into these classes:

(i) Cyclic, branched, or linear, completely fluorinated alkanes;

(ii) Cyclic, branched, or linear, completely fluorinated ethers with no unsaturations;

(iii) Cyclic, branched, or linear, completely fluorinated tertiary amines with no unsaturations; and (iv) Sulfur containing perfluorocarbons with no unsaturations and with sulfur bonds only to carbon and fluorine. Water is not a VOC.

A "high solids formulated coating composition" means an aqueous formulated coating composition containing more than about 75 weight percent solids as per ASTM test D-2369-92. "Film" is formed by application of the formulated coating composition to a base or substrate, evaporation of solvent, if present, and crosslinking.

"Dispersion" in respect to a polymeric vehicle, formulated coating composition, or components thereof means that the composition must include a liquid and particles which particles are detectable by light scattering.

"Dissolved" in respect to a polymeric vehicle, formulated coating composition or components thereof means that the material which is dissolved does not exist in a liquid in particulate form where particles larger than single molecules are detectable by light scattering.

"Soluble" means a liquid dissolved in a liquid or a solid dissolved in a liquid. "Miscible" means a liquid which is dissolved or soluble in a liquid. "Imbibe water" means a liquid is miscible with water.

"Not reactive with water" means that the constituents of the coating react slowly enough with water that the film properties are not substantially changed by water during the time and at the temperature needed for application. With the simultaneous mixing of water into a system with unblocked isocyanate and almost immediate application, the system need only be stable for about 15 seconds. The required stability of the polymeric vehicle is highly dependent upon the means of application and how quickly the polymeric vehicle or formulated coating composition is applied.

According to the invention, the amine or ammonia salt of a PHEA, such as a salt having the general formula A as set forth above permits a polymeric vehicle not only to include water, but also acts as a hardener to harden a coating binder which results upon curing a polymeric vehicle. The amine salt of the invention generally is the reaction product of a PHEA and an amine and/or ammonia.

The Amine or Ammonia Salt of the PHEA

The amine salt of the PHEA is made by mixing an amine or ammonia with a PHEA. Amines which may be used in the invention include triethylamine and dimethyl ethanol amine. It is preferred that the amino also have hydroxyl functionality. The amine salt is made by mixing about one half equal equivalent portions of the amine with the PHEA to react the phenolic hydroxyl groups on the PHEA with the amine. In any event, the amount of amine should be effective to provide dispersibility of the PHEA. In the water reducible aspect of the invention, the polymers with the carboxyl groups reactive with the amine or ammonia may be blended with the PHEA which blend then is mixed with the amine or ammonia to make a blend of water dispersible salts.

The Phenolic Ester Alcohol

The phenolic ester alcohol which is used to make the amine salt has at least one phenolic hydroxyl group, and at least one aliphatic hydroxyl group. The aliphatic hydroxyl group is primary or secondary. In an important aspect, it has two ester groups and one aliphatic hydroxyl group. Generally, it is the reaction product of a phenol carboxylic acid and an epoxy compound. In an important aspect, the phenolic ester alcohol is represented by the general formula "B"

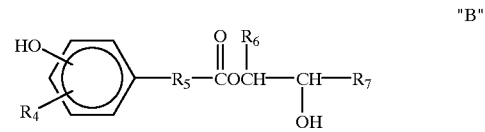

wherein $R_4$ is selected from the group consisting of hydrogen, halogen, hydroxyl, $C_1$ to $C_8$ alkyl and $C_1$ to $C_8$ alkoxy, $R_5$ is a direct bond or a $C_1$ to $C_{20}$ organic radical which may incorporate another phenol, aliphatic hydroxyl, ester, ether and/or carbonate group in its structure, $R_6$ is hydrogen or a $C_1$ to $C_{20}$ organic radical which may include an ester group, or a direct bond which may form with $R_7$ part of a 5 or 6 carbon atom cyclic ring structure, $R_7$ is $CH_2R_8$ wherein $R_8$ is selected from the group consisting of hydroxy, $OR_9$, $OOCR_{10}$ and $R_{11}$ wherein $R_9$ is a primary or secondary aliphatic group containing 3 to 20 carbon atoms which may include one or more ester linkages or an aromatic group containing 6 to 20 carbon atoms, $R_{10}$ is a primary, secondary or tertiary aliphatic group containing 4 to 20 carbon atoms which may include one or more ester linkages or an aromatic group containing 6 to 20 carbon atoms, and $R_{11}$ is a $C_2$ to $C_{20}$ organic radical which may include one or more ester linkages and where the organic radical may form with $R_6$ part of a 5 or 6 carbon atom cyclic ring structure. In a particularly important aspect $R_5$ or $R_8$ has the ester groups. The —OH expressly shown in formula B is illustrative of an aliphatic hydroxyl group.

A particularly important PHEA for use in the invention has the general formula C

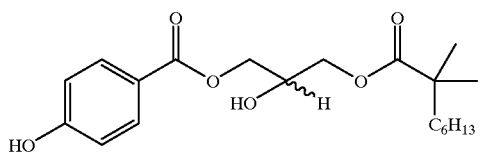

"C"

To make the PHEA, a phenol carboxylic acid reactant which may be reacted with the epoxy compound has the general formula:

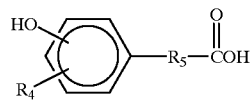

wherein $R_4$ and $R_5$ are as described above in connection with formula B. Examples of suitable phenol carboxylic acids include hydroxybenzoic acids, acids where $R_5$ is alkylene such as phenyl acetic acid, hydroxy phenyl propionic acid, hydroxyphenyl stearic acid, and acids where in $R_5$ encompasses additional phenol functionality such as 4,4-bis hydroxyphenyl pentanoic acid and the like. In a preferred embodiment of the invention, $R_4$ in formula A is hydrogen, $R_5$ is a direct bond, $R_6$ is hydrogen and $R_7$ is $CH_2OH$, a hydrocarbon moiety or an organic moiety containing ester or ether groups and containing from 1 to about 20 carbon atoms, more preferably from about 3 to 20 carbon atoms.

In an important aspect of the invention, the phenolic ester alcohol is the ester reaction product of a hydroxybenzoic acid and an epoxy compound. Suitable hydroxybenzoic acids include ortho-hydroxybenzoic acid (salicylic acid), meta-hydroxybenzoic acid and para-hydroxybenzoic acid (PHBA), with para-hydroxybenzoic acid being most preferred.

The epoxy compound may be selected from the group consisting of glycidyl esters, glycidyl alcohols, glycidyl ethers, linear epoxies and aromatic epoxies. These include glycidyl ethers of the structure:

glycidyl esters of the structure:

glycidyl or oxirane compounds having the structure:

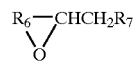

and cycloaliphatic epoxy compounds having the structures:

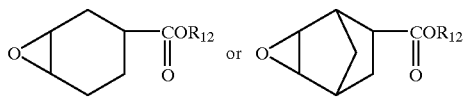

wherein $R_{12}$ is an organic radical having 1–12 carbon atoms which can include ether, ester, hydroxyl or epoxy groups.

Other epoxy materials include epoxidized alpha olefins and bis aromatic epoxies such as the reaction product of bisphenol A or F with epichlorohydrin.

Suitable epoxy compounds particularly include monoepoxides containing a terminal glycidyl group or polyepoxides containing internal oxirane or glycidyl groups or terminal glycidyl groups. Suitable epoxy compounds include glycidyl acrylate or methacrylate monomers, alkyl glycidyl ether monomers, and low molecular weight copolymers of one or more of these monomers with one or more ethylenically unsaturated monomers such as acrylates, methacrylates, vinyl aromatic monomers and the like.

Other suitable epoxy compounds include the ester reaction products of epichlorohydrin with mono- or dibasic aliphatic or aromatic carboxylic acids or anhydrides containing from about 1 to 20 carbon atoms. Inclusive of such acids are aliphatic acids such as acetic, butyric, isobutyric, lauric, stearic, maleic and myristic acids and aromatic acids such as benzoic, phthalic, isophthalic and terephthalic acids as well as the corresponding anhydrides of such acids. Preferred such acids are primary, secondary or tertiary aliphatic carboxylic acids containing from 5 to 13 carbon atoms. As described above, a very important aspect of the invention is when the epoxy compound is the glycidyl ester of a mixed aliphatic, mostly tertiary, mono carboxylic acid with an average of 9 to 11 carbon atoms such glycidyl ester being available from Exxon Chemical Co., under the trade name GLYDEXX® or from Shell Chemical Co., under the trade name CARDURA® E ester. These may be represented by the general formula "D". (Glydexx® general formula).

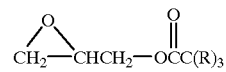

D

This aspect includes making the PHEA which is the reaction product of hydroxybenzoic acid, such as para hydroxybenzoic acid and a monoglycidyl compound having a molecular weight in the range of from about 110 to 1000 such as the monoglycidyl compound of formula D.

Still other epoxy compounds include glycidyl ether reaction products of epichlorohydrin with aliphatic or aromatic alcohols or polyols containing from about 1 to 20 carbon atoms. Suitable alcohols include aromatic alcohols such as bisphenol, bisphenol A, bisphenol F, phenolphthalein and novolac resins; aliphatic alcohols such as ethanol, isopropanol, isobutyl alcohol, hexanol, stearyl alcohol and the like; and aliphatic polyols such as ethylene glycol, propylene glycol and butylene glycol.

Other epoxy compounds which may be used include the mono-epoxides of $C_8$ to $C_{20}$ alpha mono-olefins.

The epoxy compound may also comprise epoxidized fatty compounds. Such epoxidized fatty compounds include epoxidized fatty oils, epoxidized fatty acid esters of monohydric alcohols, epoxidized fatty acid esters of polyhydric alcohols, epoxidized fatty nitriles, epoxidized fatty amides, epoxidized fatty amines and epoxidized fatty alcohols. Suitable alicyclic epoxide and polyepoxide materials include dicyclopentadiene diepoxide, limonene diepoxide, and the like. Additional useful epoxides include for example, vinyl cyclohexane dioxide, bis (3,4-epoxycyclohexyl) adipate, 3,4-epoxycyclohexylmethyl-3,4-epoxy-cyclohexane carboxylate and 2-(3,4-epoxycyclohexyl-5,5-spiro-3,4-epoxy) cyclohexane-metadioxane.

In a very important aspect of making the phenolic ester alcohol, the hydroxybenzoic acid/epoxy reaction product may be formed by reacting the hydroxybenzoic acid and the epoxy compound to provide a phenolic ester alcohol with one aliphatic hydroxyl group, optionally in a solvent therefor, at a temperature ranging from about 90° to about 120° C. to initiate such reaction. Once the reaction, by heating, it is exothermic, and the reaction temperature can rise to a temperature of about 150° to 175° C. usually without application of external heat. The reaction temperature then is maintained at about 150° C. to 170° C. (and preferably less than about 200° C.) until the reaction has been determined to be substantially complete.

Reaction products of reduced discoloration can be produced by control of the maximum temperature of the exothermic reaction. This can be achieved by a staged and/or incremental addition of one of the reactants, e.g. the epoxy reactant, so that the reaction temperature is maintained at a temperature of about 150° C. or below. The remainder of that reactant may then be added in stages or continuously while maintaining the reaction temperature below about 150° C. This process modification gives rise to reaction products having lower Color Index values.

Approximately stoichiometric quantities of the epoxy compound and the phenol carboxylic acid are used in the reaction, although a slight molar excess of epoxy may be necessary to drive the reaction to completion.

Film Forming Constituents In The Polymeric Vehicle

A. The Water-Reducible Polymeric Vehicle

In the water reducible aspect of the invention, carboxylic acid substituted polymers and oligomers are used in the invention. They are selected from the group consisting of oligoesters, oligomeric alkyds, oligomeric acrylics, oligomeric epoxies, polyesters, alkyd polymers, acrylic polymers and epoxy polymers. The oligomers and polymers have acid numbers sufficient for providing dispersibility once the polymers are converted into amine or ammonia salts. In the case of acrylics and polyesters, the acid numbers generally are in the range of from about 40 to about 60. Equal equivalent amounts of amine with polymer generally are not required to provide a dispersible salt and conversion of about 75% of the carboxyl groups on the polymer are sufficient to provide water dispersibility to the polymer. Suffice it to say, the amount of carboxyl groups converted to the salt should be effective for dispersion of the oligomer or polymer in a solvent or medium comprising water and an organic solvent. The ratio between water and organic solvent also should be effective to provide dispersibility.

In the water-reducible aspect of the invention, the polymeric vehicle includes the amine or ammonia salt of the polymeric and/or oligomeric amine or ammonia salt of the carboxylated polymer and the amine salt of the PHEA. The coating binder is obtained by curing a blend of the salt of the polymer and/or oligomer and the salt of the PHEA with an amine resin crosslinker.

The diester and polyester polyols may be prepared by well known condensation processes using a molar excess of diol. Preferably the molar ratio of diol to dicarboxylic acid is p+1:p wherein p represents the number of moles of dicarboxylic acid. The reaction may be conducted in the absence of or presence of a suitable polycondensation catalyst as is known in the art. Polyesters also can be made from carboxylic acids and oxiranes, such as

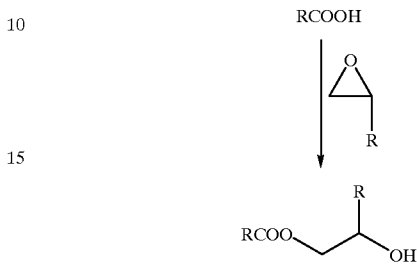

R=H, alkyl, aryl

Some preferred examples of the diols used to make the polyester polyols are one or more of the following: neopentyl glycol; ethylene glycol; hexamethylenediol; 1,2-cyclohexanedimethanol; 1,3-cyclohexanedimethanol; 1,4-cyclohexanedimethanol; diethylene glycol; triethylene glycol; tetraethylene glycol; dipropylene glycol; polypropylene glycol; hexylene glycol; 2-methyl-2-ethyl-1,3-propanediol; 2-ethyl-1,3-hexandediol; 1,5-pentanediol; thiodiglycol; 1,3-propanediol; 1,2-propanediol; 1,2-butanediol; 1,3-butanediol; 2,3-butanediol; 1,4-butanediol; 2,2,4-trimethyl-1,3-pentanediol; 1,2-cyclohexanediol; 1,3-cyclohexanediol; 1,4-cyclohexanediol; neopentyl diol hydroxy methyl isobutyrate, and mixtures thereof. Examples of polyols include triols such as glycerine, timethylol ethane, trimethylol propane, pentaerythritol and the like.

The diols are reacted with carboxyl groups to make the polyesters. The carboxyl groups may be present in the form of anhydride groups, lactone groups, or equivalent ester forming derivatives such as the acid halide or methyl ester. The dicarboxylic acids or derivatives are preferably one or more of the following: phthalic anhydride, terephthalic acid, isophthalic acid, naphthalene dicarboxylic acids, adipic acid, succinic acid, glutaric acid, fumaric acid, maleic acid, cyclohexane dicarboxylic acid, azelaic acid, sebasic acid, dimer acid, caprolactone, propiolactone, pyromellitic dianhydride, substituted maleic and fumaric acids such as citraconic, chloromaleic, mesaconic, and substituted succinic acids such as aconitic and itaconic, and mixtures thereof. Many commercially available polyesters are produced using a combination of aromatic and aliphatic dicarboxylic acids or a combination of cycloaliphatic and aliphatic dicarboxylic acids or combinations of all three types. However, where polyesters having low viscosity and low solvent content are desired, the most preferred acids used for the purposes of this invention are linear saturated or unsaturated aliphatic dicarboxylic acids having from 2 to 10 carbon atoms such as succinic, glutaric, adipic, and similar materials.

Carboxyl functional alkyd polymers may be used as the polyol component of this invention. These alkyd resins usually have a number average molecular weight in the range of from about 500 to about 20,000, are oil modified polyester resins and are broadly the product of the reaction of a dihydric alcohol and a dicarboxylic acid or acid derivative and an oil, fat or carboxylic acid derived from such oil or fat which acts as a modifier. Such modifiers are drying oils, semi-drying oils or non-drying oils. The polyhydric alcohol employed is suitably an aliphatic alcohol, and mixtures of the alcohols also may be employed. The dicarboxylic acid, or corresponding anhydrides, may be selected from a variety of aliphatic carboxylic acids or mixtures of aliphatic and aromatic dicarboxylic acids. Suitable acids and acid anhydrides include, by way of example, succinic acid, adipic acid, phthalic anhydride, isophthalic acid, trimellitic acid (anhydride) and bis 3,3', 4,4'-benzophenone tetracarboxylic anhydride. Mixtures of these acids and anhydrides may be employed to produce a balance of properties. As the drying oil or fatty acid there is suitably employed a saturated or unsaturated fatty acid of 12 to 22 carbon atoms or a corresponding triglyceride, that is, a corresponding fat or oil, such as those contained in animal or vegetable fats or oils. Suitable fats and oils include tall oil, castor oil, coconut oil, lard, linseed oil, palm oil, peanut oil, rapeseed oil, soybean oil and beef tallow. Such fats and oils comprise mixed triglycerides of such fatty acids as caprylic, capric, lauric, myristic, palmitic, and stearic and such unsaturated fatty acids as oleic, eracic, ricinoleic, linoleic and linolenic. Chemically, these fats and oils are usually mixtures of two or more members of the class. Alkyd resins made with saturated monocarboxylic acids and fats are preferable where improved weather resistance is of prime concern.

The acrylic polymers which may be used as the polyol component in the present invention are acrylic copolymer resins. The acrylic copolymer resin is prepared from at least one hydroxy-substituted alkyl (meth) acrylate and at least one non-hydroxy-substituted alkyl (meth) acrylate. The hydroxy-substituted alkyl (meth) acrylates which can be employed as monomers comprise members selected from the group consisting of the following esters of acrylic or methacrylic acid and aliphatic glycols: 2-hydroxyethyl acrylate, 3-chloro-2-hydroxypropyl acrylate; 1-hydroxy-2-acryloxy propane; 2-hydroxypropyl acrylate; 3-hydroxypropylacrylate; 2,3-dihydroxypropylacrylate; 3-hydroxybutyl acrylate; 2-hydroxybutyl acrylate; 4-hydroxybutyl acrylate; diethyleneglycol acrylate; 5-hydroxypentyl acrylate; 6-hydroxyhexyl acrylate; triethyleneglycol acrylate; 7-hydroxyheptyl acrylate; 1-hydroxy-2-methacryloxy propane; 2-hydroxypropyl methacrylate; 2,2-dihydroxypropyl methacrylate; 2-hydroxybutyl methacrylate; 3-hydroxybutyl methacrylate; 2-hydroxyethyl methacrylate; 4-hydroxybutylmethacrylate; 3,4-dihydroxybutyl methacrylate; 5-hydroxypentyl methacrylate; and 7-hydroxyheptyl methacrylate. The preferred hydroxy functional monomers for use in preparing the acrylic resins are hydroxy-substituted alkyl (meth) acrylates having a total of 5 to 7 carbon atoms, i.e., esters of $C_2$ to $C_3$ dihydric alcohols and acrylic or methacrylic acids. Illustrative of particularly suitable hydroxy-substituted alkyl (meth) acrylate monomers are 2-hydroxyethyl methacrylate, 2-hydroxyethyl acrylate, 2-hydroxybutyl acrylate, 2-hydroxypropyl methacrylate, and 2-hydroxypropyl acrylate.

Among the non-hydroxy-substituted alkyl (meth) acrylate monomers which may be employed are alkyl (meth) acrylates. Preferred nonhydroxy unsaturated monomers are esters of $C_1$ to $C_{12}$ monohydric alcohols and acrylic or methacrylic acids, e.g., methyl methacrylate, hexyl acrylate, 2-ethylhexyl acrylate, lauryl methacrylate, glycidyl methacrylate, etc. Examples of particularly suitable monomers are butyl acrylate, butyl methacrylate and methyl methacrylate.

Additionally, the acrylic copolymer resins used in the present invention may include in their composition other monomers such as acrylic acid and methacrylic acid, monovinyl aromatic hydrocarbons containing from 8 to 12 carbon atoms (including styrene, alpha-methyl styrene, vinyl toluene, t-butyl styrene, chlorostyrene and the like), vinyl chloride, vinylidene chloride, acrylonitrile, epoxy-modified acrylics and methacrylonitrile.

The acrylic copolymer preferably has a number average molecular weight not greater than about 30,000, more preferably between about 280 and about 15,000, and most preferably between about 300 and about 5000.

Carboxy substituted epoxy polymers having a number average molecular weight in the range of from about 500 to about 6,000 may be used a component of this invention.

A well known epoxy resin which may be used in the invention is made by condensing epichlorohydrin with bisphenol A, diphenylol propane which has been modified to include carboxyl groups.

The viscosity of the polymer is a function of molecular weight, the higher the molecular weight the more viscous the polymer.

Other hydroxyl-containing compounds, including resorcinol, hydroquinone, glycols, and glycerol may be used in lieu of bisphenol A.

B. The Water-Thinnable Polymeric Vehicle

In the water-thinnable aspect of the invention, the polymeric vehicle includes a polyol which may be an oligomeric oligoester or acrylic and (in an important aspect, it is an oligoester polyol) and the amine or ammonia salt of the PHEA. The polyol generally is an oligomer, however, and has an hydroxyl number effective for providing an aqueous solution of the oligomeric polyol. The coating binder is obtained by curing a blend of polyol and amine or ammonia salt of the PHEA with a crosslinker which is reactive with the hydroxyls on the polyol, the aliphatic hydroxyls on the PHEA and the hydrolysis product of the amine salt of the PHEA. The crosslinker may be an amino resin or a blocked isocyanate which is not reactive with water.

The Amino Resin Crosslinkers

Methylol (alkoxymethyl) amino crosslinking agents are suitable for use in the present invention and are well known commercial products, and are generally made by the reaction of di (poly) amide (amine) compounds with formaldehyde and, optionally, a lower alcohol. The amino resin has a crosslinking functionality of from about 3 to about 30 crosslinking groups per molecule.

Examples of suitable amino-crosslinking resins include one or a mixture of the following materials.

(a) Melamine Based Resins

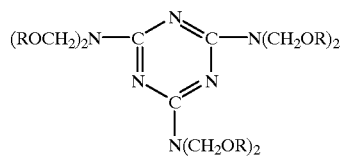

wherein R is the following:

R=$CH_3$ (Cymel® 300, 301, 303);

R=$CH_3$, $C_2H_5$ (Cymel® 1116);

R=$CH_3$, $C_4H_9$ (Cymel® 1130, 1133);

R=$C_4H_9$ (Cymel® 1156); or

R=$CH_3$, H (Cymel® 370, 373, 380, 385).

The preferred melamine is hexamethoxymethyl melamine.

(b) Benzoquanamine Based Resins

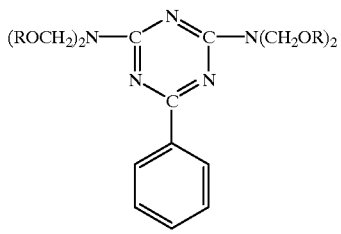

wherein R=$CH_3$, $C_2H_5$ (Cymel® 1123).

(c) Urea based resins

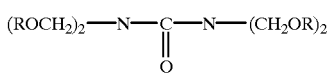

wherein:
R=$CH_3$, H (Beetle™ 60, Beetle™ 65); or
R=$C_4H_9$ (Beetle™ 80).

(d) Gycoluryl Based Resins

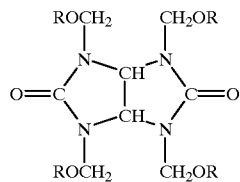

wherein:
R=$CH_3$, $C_2H_5$ (Cymel® 1171); or
R=$C_4H_9$ (Cymel® 1170).

In the water-thinnable aspect of the invention, the amino resin may be a liquid or solid. In the aspect the invention where VOCs are being minimized, if the amino resin is a solid, that solid is soluble in such blend of the polymeric vehicle and the viscosity of the formulated coating composition and polymeric vehicle should not exceed the ranges described herein. When the amino resin is a liquid, it preferably has a viscosity of less than about 3.0 Pa.s at about 25° C. A highly alkylated hexamethoxy-methylmelamine (HMMM) resin with the following general formula is a very suitable crosslinker:

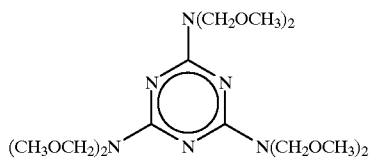

The latter HMMM resin appears to be a waxy solid under most conditions with a melting point in the range of about 30° C. and is sold by Cytec Chemical Company under the name Cymel 300. A similar crosslinker which is a melamine resin which can be used in the invention is a highly monomeric, highly methylolated hexamethylolated melamine formaldehyde resin which appears to be a solid under most conditions at 25° C. and is sold by Monsanto Chemical Company under the designation HM-2612.

Isocyanate Crosslinkers

The isocyanate crosslinkers are blocked and have an average isocyanate functionality of from about 1.9 to about 20 isocyanate groups per molecule. Isocyanate crosslinkers may be used in the water-thinnable aspect of the invention. Blocked diisocyanates which may be used as isocyanate crosslinkers in the invention include hexamethylene diisocyanate (HDI), isophorone diisocyanate (IPDI), tetramethylxylene diisocyanate (TMXDI), and other aliphatic diisocyanates such as trimethylene diisocyanate, tetramethylene diisocyanate, pentamethylene diisocyanate, 1,2-propylene diisocyanate, 2,3-butylene diisocyanate, 1,3-butylene diisocyanate, 2,4,4- or 2,2,4-trimethylhexamethylene diisocyanate; cycloalkylene diisocyanates such as 1,3-cyclopentane-diisocyanate, 1,4-cyclohexane-diisocyanate and 1,3-cyclohexane-diisocyanate; and aromatic diisocyanates such as m-phenylene diisocyanate, p-phenylene diisocyanate, 4,4'-diphenyldiisocyanate, 1,5-naphthalene diisocyanate, 4,4'-diphenylmethane diisocyanate, 2,4- or 2,6-toluene diisocyanate.

The isocyanate compound has blocked isocyanate groups. Agents which block the isocyanate groups and "deblock" at elevated temperature are known and are used in the invention. These include oxines, lactams, imines, carbamates such as acetone oxime, methyl ethyl ketoxime, and ε-caprolactam.

The polyisocyanates may be dimerized or trimerized diisocyanates such as trimerized HDI or IPDI and triisocyanates such as triphenylmethane-4,4', 4"-triisocyanate, 1,3,5-triisocyanatobenzene, 1,3,5-triisocyanatocyclohexane, 2,4,6-triisocyanatotoluene and ω-isocyanatoethyl-2,6-diisocyanatocaproate; and tetraisocyanates, such as 4,4'-diphenyldimethylmethane-2,2', 5,5'-tetraisocyanate.

They also may be polymers or copolymers with vinyl monomers of isocyanate functional monomers such as

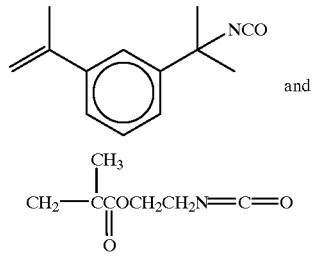

In another aspect of the invention, blocked biurets such as the biuret of hexamethylene diisocyanate (HDI) which biuret has the structure

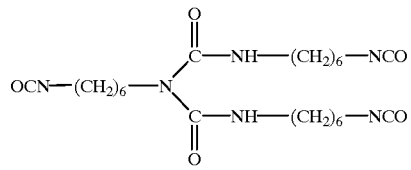

and is a trimerized product of hexamethylene diisocyanate and water may be used as polyisocyanates.

The Organic Solvent Component

The viscosity of the polymeric vehicle and the formulated coating composition is controlled with water, or in an important aspect, with a blend of water and an organic solvent which is miscible with water such as an alcohol or acetone. Acetone is useful because it is not considered a VOC. In the water-reducible aspect of the invention, the polymeric vehicle is dispersible in a medium which is a blend which generally comprises from about 40 to about 75 weight percent water. Alcohols useful in the invention include ethanol, 2-butoxyethanol, butane, amyl alcohol, tertiary butyl alcohol, butoxy propanol and propoxy propanol.

EXAMPLE I

Synthesis of the Phenolic Ester Alcohol from a Glycidyl Ester and PHBA

Into a 1 liter flask equipped with agitation, nitrogen, heating and temperature probe, 326.6 g Glydexx® N-10 glycidyl ester and 173.4 g parahydroxy benzoic (PHBA) were charged. The mixture was heated at 110° C. At that point, an exothermic reaction takes place. The maximum temperature reached was 160° C. The solution was then cooled and discharged. Physical properties are given below.

Acid Number: 0 mg KOH/gram
NVM: >99%
Color: <3 Gardner

EXAMPLE II

A. Preparation of Salt

Formulation of PHEA and dimethyl amino ethanol (DMAE) in 2-Butoxyethanol (BTE): Influence of Water Addition for Cloudiness and Phase Separation The amine salt of the PHEA of general formula C which is made as described in Example I above is made by mixing the ingredients set forth below.

| PHEA (g) | 1.02 | 1.12 | 1.02 | 1.03 | 1.03 | 1.03 |
|---|---|---|---|---|---|---|
| DMAE (g) | 0.24 | 0.25 | 0.25 | 0.23 | 0.24 | 0.24 |
| BTE (g) | 1.78 | 1.55 | 1.38 | 0.54 | 0.32 | 0.14 |
| Concn. (%)* | 41.4 | 46.9 | 47.9 | 70 | 79.8 | 90 |
| Water added to get Hazy/Cloudy solution | 6.37 | 5.52 | 5.34 | 2.04 | 1.49 | 0.82 |
| Water added for Phase separation** | 3.57 | 4.05 | 5.41 | 2.42 | 1.08 | 0.95 |

BTE - 2-Butooxyethanol.
*Concen. =[(PHEA + DMAE)/ (PHEA + DMAE + BTE)] × 100.
**Since the solution was quite cloudy, exact phase separation was difficult to be determined.

B. Preparation of Coating

Water-borne Coatings Based on PHEA and Alkyd Resin

Coatings using the amine salt as describe above were applied to panels. After application, the coatings were baked under conditions as set forth below.

| Experiment | I | II | III | IV (Control Study) |
|---|---|---|---|---|
| Short Oil Alkyd 74-7450 | 0.76 g | 0.75 g | 0.77 g | 3.00 g |
| PHEA | 0.25 g | 0.26 g | 0.25 g | — |
| Resimene 747 | 0.27 g | 0.15 g | 0.35 g | 1.08 g |
| 2-Butoxyethanol | 0.76 g | 0.31 g | 0.31 g | 0.93 g |
| 2-Dimethylaminoethanol | 0.05 g | 0.08 g | 0.06 g | 0.18 g |
| H$_2$O | 1.48 g | 1.66 g | 1.64 g | 5.10 g |
| Baking Conditions | 300° F./ 30 min. | 270° F./ 30 min. | 270° F./ 30 min. | 280° F./ 30 min. |
| Appearance of Panels* | Uniform, cloudy | Uniform, cloudy | Uniform, cloudy | Uniform, glossy with some bubbles |
| NVW (%) [-H$_2$O]** | 42.99 | 78.90 | 89.04 | 63.85 |
| Film Thickness (mil) | 0.2–0.6 | 0.5–0.8 | 0.6–1.0 | 0.7–1.0 |
| Adhesion | 5B | 5B | 5B | 5B |

| Experiment | I | II | III | IV (Control Study) |
|---|---|---|---|---|
| Pencil Hardness | 3–4H | 3H | 3H | H-2H |
| Impact Resistance - Direct (lb-in) | 50 | 140 | 160 | 80 |
| Impact Resistance - Reverse (lb-in) | <40 | 120 | 120 | <60 |
| MEK double rub resist. | >200 | >200 | >200 | >200 |

*The panels were coated on phosphated steel panels using #60 drawdown bar.
**NVW was determined at the experimental baking conditions for 1 hour.

What is claimed is:

1. A water dispersible salt which is the reaction product of a phenolic ester alcohol and an amine or ammonia about one equivalent of amine or ammonia being reacted with about every equivalent of phenolic hydroxyl group which is part of the phenolic ester alcohol to form the salt of the phenolic ester alcohol and wherein the phenolic ester alcohol has the general formula

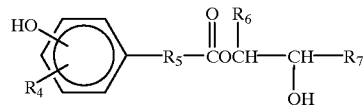

wherein R$_4$ is selected from the group consisting of hydrogen, halogen, hydroxyl, C$_1$ to C$_8$ alkyl and C$_1$ to C$_8$ alkoxy, R$_5$ is selected from the group consisting of a direct bond, C$_1$ to C$_{20}$ organic radical having only carbon and hydrogen atoms, a C$_1$ to C$_{20}$ organic radical which includes in its structure a substitution group selected from the group consisting of phenol, aliphatic hydroxyl, ester, ether, carbonate and combinations thereof in its structure, R$_6$ is selected from the group consisting of hydrogen, a C1 to C20 organic radical, a C1 to C20 organic radical which includes in its structure at least one ester linkage or a direct bond which forms with R$_7$ part of a 5 or 6 carbon atom cyclic ring structure, R$_7$ is CH2R8 wherein R$_8$ is selected from the group consisting of hydroxy, OR$_9$, OOCR$_{10}$ and R$_{11}$ wherein R$_9$ is selected from the group consisting of a primary aliphatic group containing 3 to 20 carbon atoms, a secondary aliphatic group containing 3 to 20 carbon atoms, an aromatic group containing 6 to 20 carbon atoms, a primary aliphatic group containing 3 to 20 carbon atoms which includes at least one ester linkage and a secondary aliphatic group containing 3 to 20 carbon atoms which includes at least one ester linkage, wherein R$_{10}$ is selected from the group consisting of a primary aliphatic group containing 4 to 20 carbon atoms, a secondary aliphatic group containing 4 to 20 carbon atoms, a tertiary aliphatic group containing 4 to 20 carbon atoms, an aromatic group containing 6 to 20 carbon atoms, and combinations thereof wherein the primary, secondary and tertiary aliphatic groups include at least one ester linkage, and R11 is selected from the group consisting of a C2 to C20 organic radical, a C2 to C20 organic radical which includes in its structure at least one ester linkage, a C2 to C20 organic radical which forms with R6 part of a 5 or 6 carbon atom cyclic ring structure, and combinations thereof.

2. A salt as recited in claim 1, wherein the phenolic ester alcohol has the general formula.

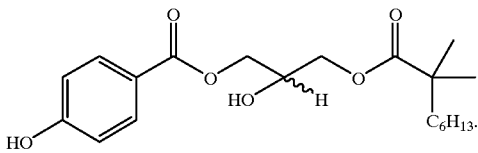

3. A water dispersible salt which is the reaction product of a phenolic ester alcohol and an amine or ammonia, the phenolic ester alcohol having one phenolic end having not more than two phenolic hydroxyls, and the phenolic ester alcohol having at least one aliphatic hydroxyl and two ester groups, about one equivalent of amine or ammonia being reacted with about every equivalent of phenolic hydroxyl group which is part of the phenolic ester alcohol to form the salt of the phenolic ester alcohol, the amine or ammonia salt formed at one or more of the phenolic hydroxyls of the phenolic ester alcohol.

4. A salt as recited in claim 3 wherein the phenolic end of the phenolic ester alcohol has one phenolic hydroxyl.

5. A salt as recited in claim 3 wherein phenolic ester alcohol has at least two ester groups.

6. A salt as recited in claim 3 wherein the phenolic end of the phenolic ester alcohol has one phenolic hydroxyl para to an ester group.

7. A salt as recited in claim 3 wherein the phenolic ester alcohol has at least two ester groups, the phenolic end of phenolic ester alcohol has one phenolic hydroxyl which is para to at least one of the ester groups.

8. A salt as recited in claims 3, 4, 5, 6 or wherein the phenolic ester alcohol is mixed with an amine or ammonia, the amine or ammonia being in an amount effective to make the salt dispersible in a solvent which includes at least 3 weight percent water.

9. A salt as recited in claim 8 wherein at least about one half equivalent of the amine or ammonia is mixed with every equivalent of phenolic hydroxyl present from the phenolic ester alcohol.

10. A salt as recited in claim 8 wherein the salt is dispersible in a solvent which includes at least about 40 weight percent water.

11. A water dispersible salt having the general formula

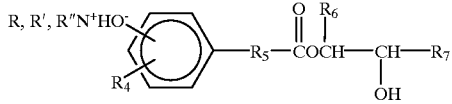

wherein $R_4$ is selected from the group consisting of hydrogen, halogen, hydroxyl, $C_1$ to $C_8$ alkyl and $C_1$ to $C_8$ alkoxy, $R_5$ is selected from the group consisting of a direct bond, $C_1$ to $C_{20}$ organic radical having only carbon and hydrogen atoms, a $C_1$ to $C_{20}$ organic radical which includes in its structure a substitution group selected from the group consisting of phenol, aliphatic hydroxyl, ester, ether, carbonate and combinations thereof in its structure, $R_6$ is selected from the group consisting of hydrogen, a $C_1$ to $C_{20}$ organic radical, a $C_1$ to $C_{20}$ organic radical which includes in its structure at least one ester linkage or a direct bond which forms with $R_7$ part of a 5 or 6 carbon atom cyclic ring structure, $R_7$ is $CH_2R_8$ wherein $R_8$ is selected from the group consisting of hydroxy, $OR_9$, $OOCR_{10}$ and $R_{11}$ wherein $R_9$ is selected from the group consisting of a primary aliphatic group containing 3 to 20 carbon atoms, a secondary aliphatic group containing 3 to 20 carbon atoms, an aromatic group containing 6 to 20 carbon atoms, a primary aliphatic group containing 3 to 20 carbon atoms which includes at least one ester linkage and a secondary aliphatic group containing 3 to 20 carbon atoms which includes at least one ester linkage, wherein $R_{10}$ is selected from the group consisting of a primary aliphatic group containing 4 to 20 carbon atoms, a secondary aliphatic group containing 4 to 20 carbon atoms, a tertiary aliphatic group containing 4 to 20 carbon atoms, an aromatic group containing 6 to 20 carbon atoms, and combinations thereof wherein the primary, secondary and tertiary aliphatic groups include at least one ester linkage, and $R_{11}$ is selected from the group consisting of a $C_2$ to $C_{20}$ organic radical, a $C_2$ to $C_{20}$ organic radical which includes in its structure at least one ester linkage, a $C_2$ to $C_{20}$ organic radical which forms with $R_6$ part of a 5 or 6 carbon atom cyclic ring structure, and combinations thereof, and $R_{12}$ is selected from the group consisting of hydrogen, alkyl, —OH and mixtures thereof, and R, R' and R" are alkyl, hydroxyl substituted alkyl, and H.

12. A water dispersible salt as recited in claim 11, wherein the alkyl of R, R' and R" has 4 or less carbon atoms.

13. A water dispersible salt as recited in claims 11 or 12, where the compound as the general formula

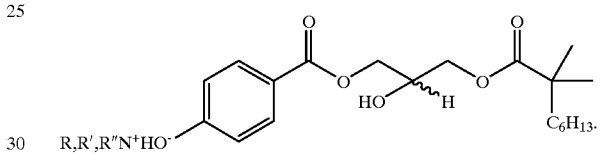

14. A water dispersible amine or ammonia salt of a phenolic ester alcohol, the phenolic ester alcohol having one phenolic end having not more than two phenolic hydroxyls, and the phenolic ester alcohol having at least one aliphatic hydroxyl and two ester groups, the amine or ammonia salt formed at one or more of the phenolic hydroxyls of the phenolic ester alcohol.

15. An amine or ammonia salt as recited in claim 14 wherein the phenolic end of the phenolic ester alcohol has one phenolic hydroxyl.

16. An amine or ammonia salt as recited in claim 14 wherein phenolic ester alcohol has at least two ester groups.

17. An amine or ammonia salt as recited in claim 14 wherein the phenolic end of the phenolic ester alcohol has one phenolic hydroxyl para to an ester group.

18. An amine or ammonia salt as recited in claim 14 wherein the phenolic ester alcohol has at least two ester groups, the phenolic end of phenolic ester alcohol has one phenolic hydroxyl which is para to at least one of the ester groups.

19. A water dispersible salt having the general formula

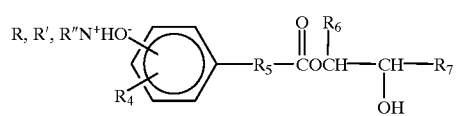

wherein R, R' and R" are alkyl, hydroxyl substituted alkyl, and H.

20. A water dispersible salt as recited in claim 19, wherein the alkyl of R, R' and R" has 4 or less carbon atoms.

* * * * *